United States Patent
Pindiprolu et al.

(10) Patent No.: US 9,038,450 B2
(45) Date of Patent: May 26, 2015

(54) METHOD AND APPARATUS FOR CHARACTERIZING FLUID CHANNELING THROUGH A CEMENT FORMATION INTERFACE OF A SUBTERRANIAN WELLBORE

(71) Applicant: HALLIBURTON ENERGY SERVICES, INC., Houston, TX (US)

(72) Inventors: Sairam K S Pindiprolu, Pune (IN); Abhinandan Chiney, Mahasrashtra (IN); Venkata Gopala Rao Palla, Pune (IN)

(73) Assignee: Halliburton Energy Services, Inc., Houston, TX (US)

( * ) Notice: Subject to any disclaimer, the term of this patent is extended or adjusted under 35 U.S.C. 154(b) by 238 days.

(21) Appl. No.: 13/745,456

(22) Filed: Jan. 18, 2013

(65) Prior Publication Data

US 2014/0202690 A1     Jul. 24, 2014

(51) Int. Cl.
  *E21B 49/02* (2006.01)
  *G01N 15/08* (2006.01)
  *E21B 33/13* (2006.01)
  *E21B 33/14* (2006.01)

(52) U.S. Cl.
  CPC ............ *G01N 15/0826* (2013.01); *E21B 33/13* (2013.01); *E21B 33/14* (2013.01)

(58) Field of Classification Search
  CPC .......................... G01N 15/082; G01N 15/0806
  USPC ................................................. 73/38, 152.07
  See application file for complete search history.

(56) References Cited

U.S. PATENT DOCUMENTS

| | | | | |
|---|---|---|---|---|
| 2,618,151 A | * | 11/1952 | Leas | 73/38 |
| 2,737,804 A | * | 3/1956 | Herzog et al. | 73/38 |
| 4,304,122 A | * | 12/1981 | Tentor | 73/38 |
| 4,753,107 A | * | 6/1988 | Reed et al. | 73/38 |
| 4,827,761 A | * | 5/1989 | Vinegar et al. | 73/38 |
| 6,178,808 B1 | * | 1/2001 | Wang et al. | 73/38 |
| 2004/0094298 A1 | | 5/2004 | Tare et al. | |
| 2006/0225523 A1 | | 10/2006 | Reddy et al. | |
| 2008/0178683 A1 | | 7/2008 | Heathman et al. | |
| 2011/0061525 A1 | | 3/2011 | Gray et al. | |
| 2011/0094295 A1 | | 4/2011 | Meadows et al. | |
| 2013/0340505 A1 | * | 12/2013 | Go Boncan et al. | 73/38 |

OTHER PUBLICATIONS

International Search Report dated Mar. 20, 2014 for Application No. PCT/US13/071197.
Written Opinion dated Mar. 20, 2014 for Application No. PCT/US13/071197.

(Continued)

*Primary Examiner* — John Fitzgerald
(74) *Attorney, Agent, or Firm* — John W. Wustenberg; Baker Botts L.L.P.

(57) ABSTRACT

Disclosed is an apparatus and method for testing a cemented bonding with the formation under wellbore pressure conditions. The apparatus comprises a pressure chamber containing a core of formation material. The cement material to be tested is allowed to set or bond to one side of the core while formation fluids under wellbore pressure conditions are present on the other side. Leakage of formation fluids is measured to evaluate the quality of the interface between the cement and formation materials.

20 Claims, 4 Drawing Sheets

(56) References Cited

OTHER PUBLICATIONS

Yong Ma, Maorong Cui, Xiaoyang Guo, "How to Evaluate the Effect of Mud Cake on Cement Bond Quality of Second Interface?," SPE/IADC 108240, SPE/IADC Middle East Drilling Technology Conference and Exhibition, Cairo, Egypt, Oct. 22-24, 2007, 6 pages.

H.K.J ;Adva, B. Craster, T.G.J. Jones, G. Goldsmith, D. Scott, "The Cement-to-Formation Interface in Zonal Isolation," IADC/SPE 88016, IADC/SPE Asia Pacific Drilling Technology Conference and Exhibition, Kuala Lumpur, Malaysia, Sep. 13-15, 2004, 14 pages.

James E. Griffith, Samuel Osisanya, "Thickness Optimization of Drilling Fluid Filter Cakes for Cement Slurry Filtrate Control and Long-Term Zonal Isolation," SPE 29473, 1995 SPE Production Operations Symposium, Apr. 2-4, 1995, 8 pages.

G. Maserati, E. Daturi, A. Belloni, L. Del Gaudio, S. Bolzoni, W. Lazzari, and G. Leo, "Nano-emulsions as Cement Spacer Improve the Cleaning of Casing Bore During Cementing Operations," SPE 133033, SPE Annual Technical Conference and Exhibition, Florence, Italy, Sep. 19-22, 2010, 10 pages.

* cited by examiner

METHOD AND APPARATUS FOR CHARACTERIZING FLUID CHANNELING THROUGH A CEMENT FORMATION INTERFACE OF A SUBTERRANIAN WELLBORE

CROSS REFERENCE TO RELATED APPLICATIONS

None.

BACKGROUND

1. Technical Field

The present invention relates to equipment and methods used in testing the aspects of the cement-formation interface and quantifying the fluid influx through the interface between the formation and cement in a wellbore at a subterranean location.

2. Background Art

In the process of drilling and completing hydrocarbon wells, it is common place to install heavy steel casing in a well and to place cement between the casing and the well bore wall at a subterranean location to anchor the casing in place and prevent migration of fluids along the annulus outside the casing.

Cementing is a common well operation. For example, hydraulic cement compositions can be used in cementing operations in which a string of pipe, such as casing or liner, is cemented in a wellbore. Cementing materials used in wells comprise a slurry of Portland cement, water and sometimes one or more additives. Additives include accelerators (such as calcium chloride), weighting materials (such as barium sulfate), retarders (such as gypsum), light weight additives (such as bentonite), and a variety of lost-circulation materials (such as mica flakes). As used herein the term "cement slurry" refers to a mixture of cement and water in a form that can be pumped into the well to allow to set or hardened.

Cement used to stabilize the pipe in the wellbore and prevents undesirable migration of fluids along the annulus between the wellbore and the outside of the casing or liner between various zones of subterranean formations penetrated by the wellbore. Where the wellbore penetrates into a hydrocarbon-bearing zone of a subterranean formation, the casing can later be perforated to allow fluid communication between the zone and the wellbore. The cemented casing is intended to enable subsequent or remedial separation or isolation of one or more production zones of the wellbore, for example, by using downhole tools such as packers or plugs, or by using other techniques, such as forming sand plugs or placing cement in the perforations.

In performing cementing, a hydraulic cement composition is pumped as a fluid (typically in the form of suspension or slurry) into a desired location in the wellbore. For example, in cementing a casing or liner, the hydraulic cement composition is pumped into the annular space between the exterior surfaces of a pipe string and the borehole (that is, the wall of the wellbore). The cement composition is allowed time to set (harden) in the annular space, thereby forming an annular sheath of hardened, substantially impermeable cement. The hardened cement is provided to support and position the pipe string in the wellbore and to fill the annular space between the exterior surfaces of the pipe string and the borehole of the wellbore.

Poor bonding between the cement and the wellbore formation wall especially at the location of the hydrocarbon bearing formation can cause problems. Poor bonding with the formation material can be caused by a variety of reasons. As used herein the term "bond" as used in this context refers to the adhering or joining of the cement to the formation materials exposed in the wellbore wall. The area of contact between the cement and the formation material is referred to as the cement formation interface.

Poor nucleation causes the interaction between the cement particles themselves to be much higher than the interaction between the cement and the formation. This leads to very poor bonding of the cement with the formation.

If the well is in an underbalanced state prior to cementing, the exposed surface of the formation at the wellbore often has a thin layer of this formation fluid. The term "formation fluids" is used herein to refer to naturally occurring fluids present in the formation, such as, hydrocarbons, salt water, liquefied gases and other liquids. This layer of formation fluids interferes and has a detrimental effect on the bonding between the cement and the formation material and renders the combination incompatible.

Often HPHT (high pressure high temperature) wells (for example 350F. and 12,000 psi) require heavier cements that inherently have low water content. This sometimes causes low bonding because there is not sufficient water to keep the tensile stresses in the cement sheath under the threshold value to avoid deboning.

It is common for the wellbore to penetrate subterranean zones of formation materials, such as, shale. Shale, in the presence of freshwater expands, destabilizes and crumbles. This causes the formation at the interface to cave in leaving gaps or voids between the shale formation and cement. As used herein the "formation materials" refers to subterranean materials present at the wellbore wall.

Filter cake is often left behind on the formation at the wellbore. This filter cake remains in place after cementing and forms as a permeable layer between the cement and formation. This filter cake material forms a pathway for the fluid to migrate axially through the cement. This will also make the formation devoid of a strong chemical bond with the cement.

When Oil Based Drilling Fluids are used, incomplete surface cleaning with a surfactant-laden spacer either due to lack of sufficient shear rates, contact time or surfactant concentrations may leave a non-polar film that comes in between the cement and the wellbore surface.

The poor bond formation provides a path of low resistance for the formation fluid which is at a considerable high pressure to leak along the well bore between formations to zones. This prevents effective zonal isolation and build up pressure in the annulus of the wellbore.

There has been a long felt need in the industry for developing a method for characterizing the channeling of formation fluids through the interface between the setting cement and the formation. The challenge here is to quantify the fluid influx due to channeling during the entire process of setting of the cement through the cement-formation interface. In the present invention, an apparatus and characterization technique is designed to identify this process quantitatively.

SUMMARY OF THE INVENTIONS

The present invention provides an improved apparatus and method for use in testing cement-formation bonding under wellbore conditions.

BRIEF DESCRIPTION OF THE DRAWINGS

The drawing is incorporated into and forms a part of the specification to illustrate at least one embodiment and example of the present invention. Together with the written description, the drawing serves to explain the principles of the invention. The drawing is only for the purpose of illustrating at least one preferred example of at least one embodiment of the invention and is not to be construed as limiting the invention to only the illustrated and described example or examples. The various advantages and features of the various embodiments of the present invention will be apparent from a consideration of the drawing in which.

DETAILED DESCRIPTION

Figure 1:
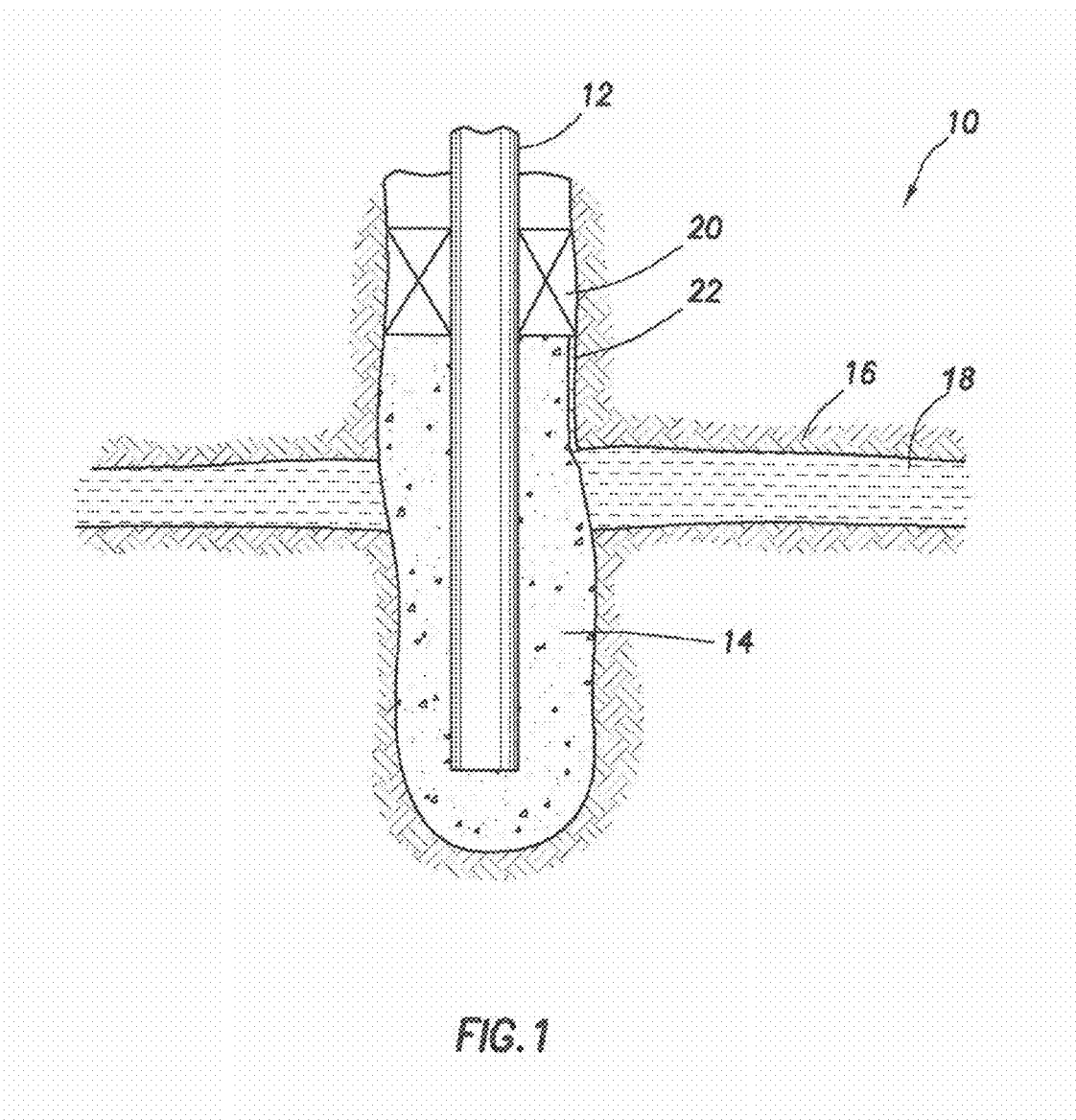
FIG. 1 are a longitudinal section view of a portion of a cemented wellbore formation interface.

Referring now to the drawings wherein like reference characters are used throughout the several views there is illustrated in FIG. 1 a cross-sectional view of typically cemented wellbore system which for descriptive purposes will be referred to by reference numeral 10. In FIG. 1 the wellbore is illustrated as the bottom of a cemented wellbore with a poor bond with lateral leakage. It is anticipate that the problem could also be present in the situation where cementing was performed at an up-hole location.

In FIG. 1 cement 14 has been placed in the annulus around the casing 12 and the cement 14 is in the process of gelling (hardening). The cement is in contact with a porous formation 16 saturated with reservoir fluid 18. The formation 16 is at down-hole pressure and temperature. In HTHP wells the pressure can be for example 12,000 psi or higher. The presence of poor bond between the cement 14 and the formation 16 can be as a result of the one or many of the phenomena discussed in the foregoing discussion. It is difficult to predict the performance of a cement to bond with the formation at wellbore conditions. A poor bond between the cement 14 and formation 16 can lead to a leak path along the cement interface with the formation. This leak path allows formation fluid to escape the surrounding zones.

Typically cement is pumped down the well-bore and into the annulus as illustrated in FIG. 1. The spacer fluid 20 is used to physically isolate one special-purpose fluid from another. It may be undesirable for one special-purpose fluid to mix with another used in the well, so a spacer fluid compatible with each is used between the two. A spacer fluid is usually used when changing between well fluids used in a well. In this case the spacer fluid 20 is used to separate the cement slurry from other fluids in the wellbore.

Figure 2:
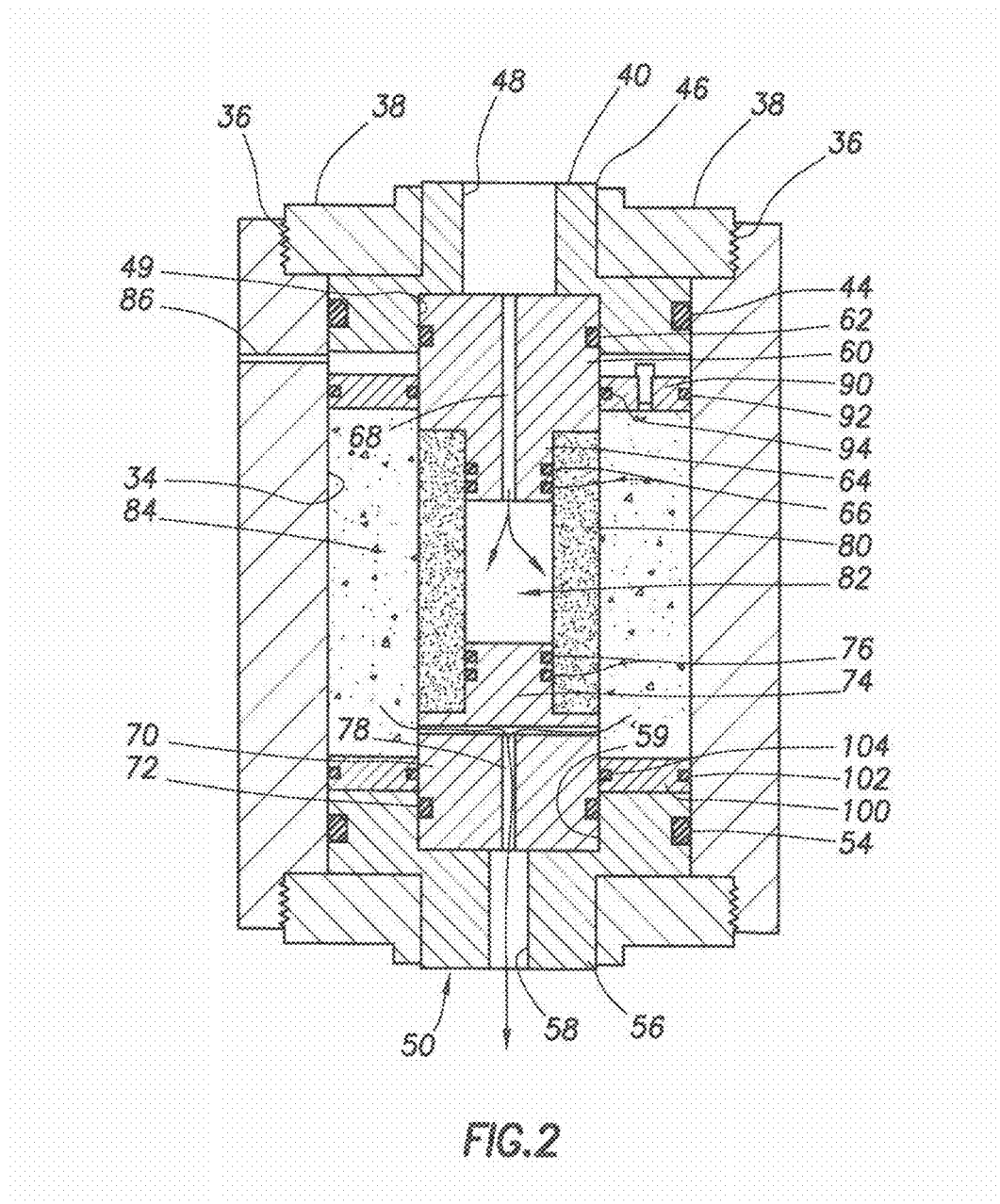
FIG. 2 is a longitudinal cross sectional view of the apparatus for testing and qualifying the interface between the cement material and the formation material according to the present invention.

The present invention provided an apparatus and means to test for the problem illustrated in FIG. 1, under well-bore conditions. In FIG. 2, the test fixture 30 of the present invention is illustrated in diagramic form.

For example, a spacer fluid is used to change from a drilling fluid during drilling to cement composition during cementing operations in the well. In case of an oil-based drilling fluid, it should be kept separate from a water-based cementing fluid. In changing to the latter fluid, a chemically treated water-based spacer fluid is usually used to separate the drilling fluid from the water-based cementing fluid.

There has been a long felt need in the industry for equipment and methods for testing and characterizing formation fluids channeling at the interface of the setting cement and the formation. There is a need to quantify fluid influx at the cement-formation interface during the entire process of setting of the cement. In the present invention, an apparatus and characterization technique is designed to test fluid influx process quantitatively under subterranean wellbore conditions. The present invention provides an apparatus and method for testing fluid influx in setting cement using formation rock under wellbore pressures.

Turning now to FIG. 2, a formation interface test apparatus or test fixture 30 is illustrated. The fixture 30 is configured to replicate the downhole conditions illustrated and described in reference to FIG. 1. The test fixture 30 comprises a pressure vessel 32, which in the current embodiment is cylindrical in shape. The pressure vessel 32 is of sufficient burst strength to safely accommodate internal test pressures mimicking those present at a subterranean wellbore conditions. Ideally, the vessel could be constructed to withstand pressures in excess of 12,000 to 14,000 psi, although for lower pressure applications, the vessel need not withstand these high pressures. In this embodiment, the inner surface 34 of the pressure vessel 32 is smooth to accommodate annular seals. The ends are counter-bored and internally threaded at 36 for use in installing end caps 38. The end caps 38 and the thread 36 are sufficient strength to withstand the forces generated by pressurizing the pressure vessel 32 two subterranean wellbore pressures.

Upper and lower pressure bulkheads 40 and 50, respectively, are positioned inside the wellbore adjacent to end caps 36. The terms upper and lower are used herein to indicate position shown on the drawing and are not intended to imply that the parts of the apparatus will be used in any particular orientation. The upper and lower pressure bulkheads 40 and 50 seal against the pressure vessels inner surface 34. As illustrated the bulkheads have annular seals 44 which can be in the form of O-rings or annular packing suitable for sealing the pressures present in the pressure vessel 32. The upper pressure bulkhead 40 has a neck portion 44 that extends through an opening in the end cap 38. A bore 48 extends axially through the neck portion 44 from the exterior of the pressure vessel 32. An enlarged counter bore 49 extends into the upper pressure bulkhead 40 from the interior the pressure vessel 32.

The lower pressure bulkhead 50 is basically of the same construction. The upper pressure bulkhead 40, with a seal 54, neck 56, bore 58 and counter bore 59. As illustrated in the lower pressure bulkhead 50 the bore 58 is smaller than the bore 48 in the upper pressure bulkhead 40.

Upper and lower core mounting fixtures 60 and 70 are positioned in counter bores 49 and 59, respectively. Annular seals and 62 and 72, seal against the walls of the counter bores 49 and 59, respectively. The core mounting fixtures 60 and 70 each have produced necked down cylindrical shaped portions 64 and 74. These portions 64 and 74 are shaped to fit into the ends of a cylindrical formation core 80. Annular seals 66 on portion 64 seal against the interior core 80 and seals and 76 on portion 74 seal against the interior of the core 80.

As illustrated in FIG. 2, a cylindrical chamber 82 is defined by the interior wall of the core 80 and the portions 64 and 74. A chamber 84 is formed on the outside of the core 80. Chamber 84 is formed between the exterior wall of the core 80, the interior wall 34 of the pressure vessel. The ends of this chamber 84 the closed off by the upper and lower pressure bulkhead 40 and 50. A passageway 86 extends through the wall of the pressure vessel 32 to connect the interior chamber 84 with the exterior of the vessel 32.

A passageway 68 in the upper core mounting fixture 60 connects bore 48 with chamber 82. A passageway 78 in the lower core mounting fixture 70 connects bore 58 with chamber 84.

Figure 4:
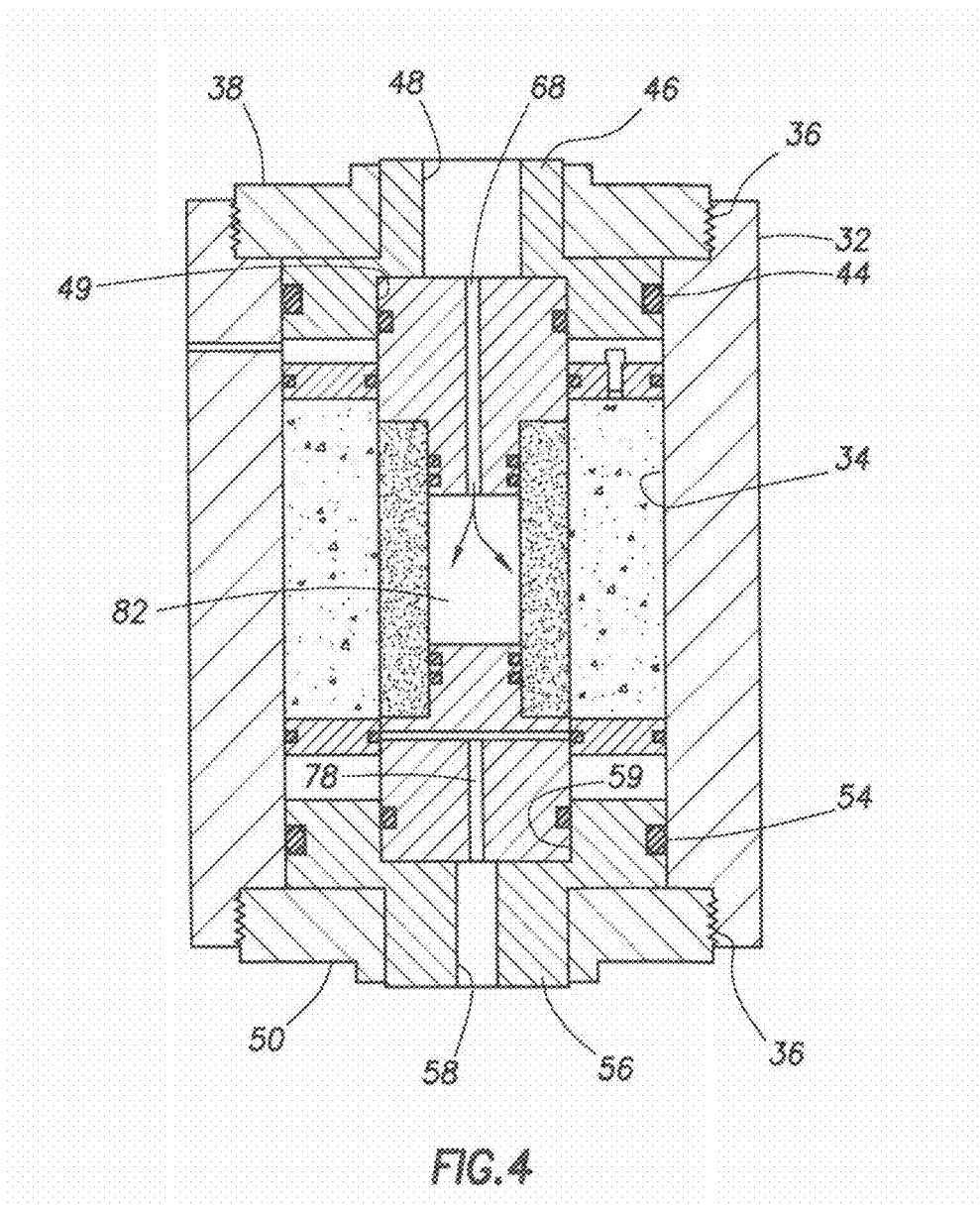
FIG. 4 is a longitudinal cross sectional view similar to FIG. 2, illustrating an alternative cement bond testing set up.

Two annular shaped pistons 90 and 100 are positioned in the chamber 84 to seal against an interior wall 34 of the pressure vessel 30. The piston 90 is positioned to slide along and seal against the outer surface of the upper core mounting fixtures 60. Suitable annular seals 92 and 94 are provided to enhance sealing. Piston 100 is positioned to slide along to seal against the outer surface of the lower core mounting fixture 70. Suitable annular seals 102 and 104 to enhance sealing. In FIG. 2 piston 100 is positioned below the points where passageway 78 enters chamber 84. In FIG. 4 piston 100 is positioned above the points where passageway 78 enters chamber 84.

Figure 3:
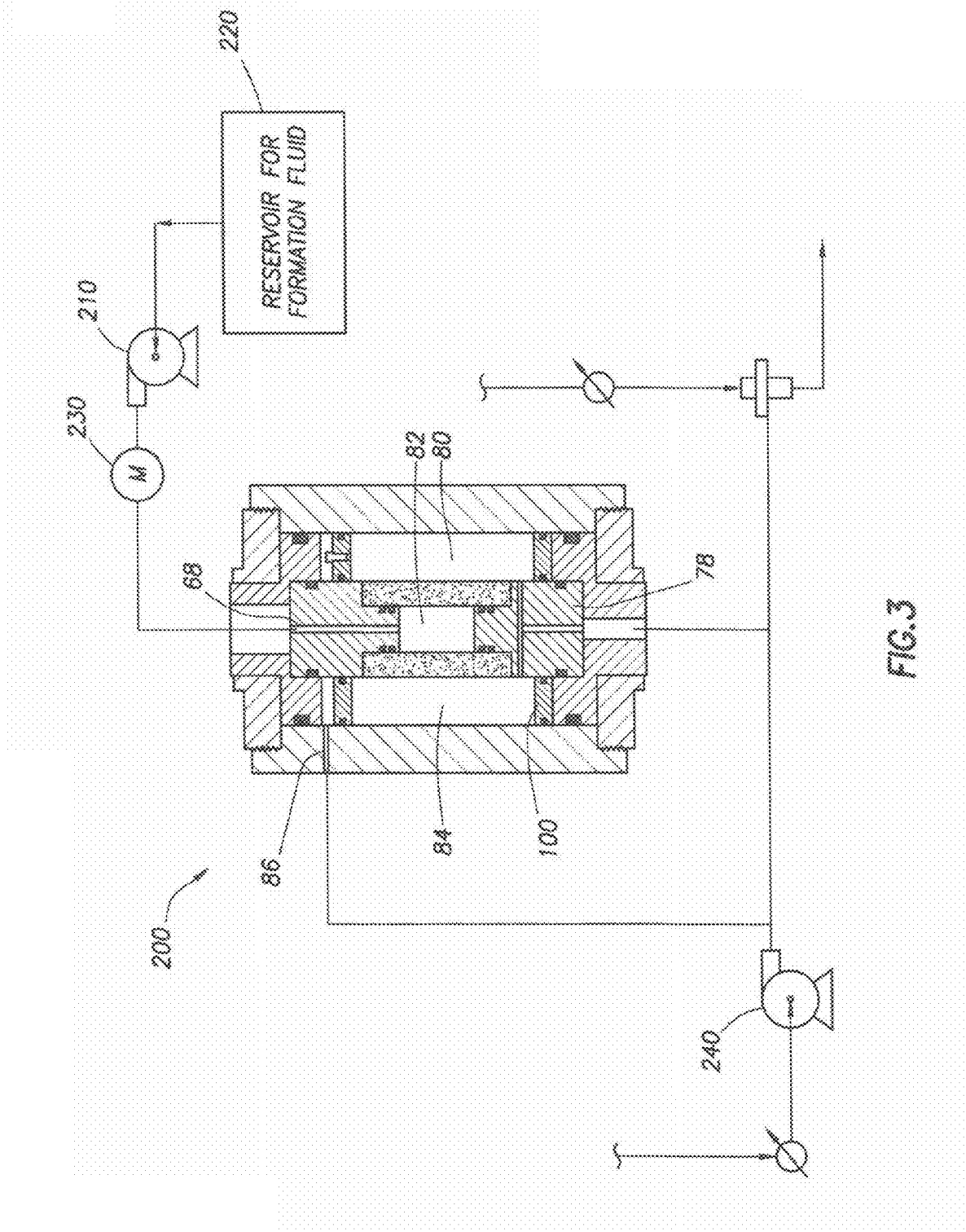
FIG. 3 is a piping diagram illustrating the system for quantifying the interface between the cement material and the formation material according to the present invention.

Turning now to FIG. 3, a system 200 for using the test fixture 30 is illustrated. It is noted that the test fixture 30 is in the configuration illustrated in FIG. 2 with the piston 100 below the point where passageway 78 enters chamber 84. A cylindrical core 80 with an internal chamber 82 is positioned in chamber 84. The core 80 is formed from material either identical to or approximating the formation to which the cement bonding is to be applied. The chamber 84 surrounding the core is filled with the wet cemented to be tested.

The passageway 68 is connected to the high side of a fluid pump 210 which is connected to a tank to 220 containing a reservoir of formation fluid. Pump 210 is preferably a constant pressure upon which delivers formation fluid to the passageway 68 and the chamber 82 inside the formation sample 80. A flow meter 230 measures formation fluid flow into the chamber 82. Pump 210 is set to maintain the formation fluid in the chamber 82 and a pressure equal to the formation pressure at the location in the world where the cement is to be bonded to the core material.

Passageways 78 and 86 are connected to a second fluid pressure pump 240 which maintains pressure on the cemented chamber 84 while it sets up and forms a bond against exterior wall of the core 80. Suitable pressure regulators the present to control the pump 242 maintain a controlled pressure on the cement.

The system 200 is designed such that the chamber 82 in the core 80 is maintained at a constant pressure and contains the reservoir fluid laced with a tracer that can be identified. Tracer identification includes using known analytic techniques that may include and is not restricted to UV-Vis Spectrophotometry and Titration. This chamber 82 is connected to reservoir 220 of reservoir fluid which mimics the infinite reservoir encountered in the wellbore. Core chamber 82 is surrounded by an annular region which contains cement slurry maintain at a pressure that replicates the pressure encountered in actual wellbore conditions. Chamber 84 containing the cement are in surface contact with the porous rock core (natural or artificial with known permeability) bearing the characteristics of the formation rock.

In one embodiment (FIG. 4), a passageway is present to allow for the migration of reservoir fluid from the cement chamber 84 into passageway 78 and out to a collector for further analysis. This passageway is maintained pressurized using a fluid source 240 and is kept at the same pressure as the cement chamber 84. This is done to prevent leakage of cement slurry into this passageway 78 to clogging it. A pressure gradient between the constant pressure reservoir and the cement chamber will cause reservoir fluid from the central core 82 to seep into the cement chamber 84. This fluid can either diffuse further into the cement or run off along the micro-annulus formed because of a poorly formed bonding between the cement and the rock core.

The production of formation fluid from passageway 78 is an indication of a poor cement bond. This poor bond formation may be deliberately created during experimentation, as can be any of the causes of poor bond formation listed in the forgoing discussion. The poorly formed interface will provide a path of lower resistance for the reservoir leading to most of the fluid to run off along this path as compared to the bulk of the cement. How the bond becomes packed and strong over time is inferred from the flow data in this set up.

Accordingly, this apparatus design is suitable to replicate the cement sections where there is a chance of cement having a constant supply of water from the annulus to compensate for volume changes in the hydration process.

In another embodiment (FIG. 3), a movable piston is placed above the passageway 78 for the fluid outlet. The length between piston and the outlet channel is kept long enough so that the piston has considerable room to move without hitting the base. When the reservoir fluid seeps into the cement chamber through the porous rock separating the two chambers, an additional pressure is generated in this chamber. It is also noted that as in the previous embodiment, the pressure at the two pistons encompassing the cement is kept the same. With the reservoir fluid seeping into the cement chamber 80, the pressure increases. In an attempt to balance this increase in pressure in the chamber 84, piston 100 moves down. This leads it to push some of the pressurizing fluid out via a constant back pressure regulator into a drain. A simple correlation between the amount of fluid influx and the amount of drain will allow the exact calculation of the reservoir fluid influx. This embodiment is ideal to replicate sections in the cement slurry that do not have access to water during hydration process.

In another embodiment, the pressure in the interior of the formation material is raised above the pressure in the cement slurry chamber while the cement hardens. This embodiment replicates cementing in an underbalanced well condition. In a different embodiment, pressure in the cement slurry chamber is maintained at a pressure higher than the pressure of the interior of the formation material.

While an element that provides directional application of force in one direction and is allowed to slip in the return direction is required, it may be incorporated in multiple ways, the application of threads has been recently used and is therefore the preferred embodiment. Additional methods may be used including roller bearings for example, possibly a helical spring wound around a mandrel, or even a rubber/metal hybrid element to provide a gripping means upon application of pressure and release upon release of pressure.

While compositions and methods are described in terms of "comprising," "containing," or "including" various components or steps, the compositions and methods also can "consist essentially of" or "consist of" the various components and steps. As used herein, the words "comprise," "have," "include," and all grammatical variations thereof are each intended to have an open, non-limiting meaning that does not exclude additional elements or steps.

Therefore, the present inventions are well adapted to carry out the objects and attain the ends and advantages mentioned, as well as, those which are inherent therein. While the invention has been depicted, described, and is defined by reference to exemplary embodiments of the inventions, such a reference does not imply a limitation on the inventions, and no such limitation is to be inferred. The inventions are capable of considerable modification, alteration, and equivalents in form and function, as will occur to those ordinarily skilled in the pertinent arts and having the benefit of this disclosure. The depicted and described embodiments of the inventions are exemplary only, and are not exhaustive of the scope of the inventions. Consequently, the inventions are intended to be limited only by the spirit and scope of the appended claims, giving full cognizance to equivalents in all respects.

Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

The invention claimed is:

1. A method for qualifying the fluid influx through the interface between the cement material to a formation material that is exposed to formation fluids at pressures present in a wellbore at a subterranean location, comprising the steps of:
    providing a pressure vessel;
    creating a formation interface in the vessel between a slurry of the cement material and the formation material;
    maintaining the pressure in the vessel above atmospheric pressure while allowing the cement material to harden; and
    measuring the quantity of fluid that has seeped in through the interface.

2. The method according to claim 1, wherein the formation material is rock.

3. The method according to claim 1, additionally comprising the step of contacting the formation material with formation fluid while hardening the cement material.

4. The method according to claim 3, wherein the formation fluid and cement slurry are maintained at the same pressure while the cement hardens.

5. The method according to claim 3, wherein the formation fluid and cement slurry are maintained at the different pressures while the cement hardens.

6. The method according to claim 3, wherein the formation fluid is maintained at a pressure higher than the pressure of the cement slurry while the cement hardens.

7. The method according to claim 3, wherein the formation fluid is maintained at a pressure lower than the pressure of the cement slurry while the cement hardens.

8. The method according to claim 1, wherein the step of creating a cement formation material interface comprises inserting a cylindrical shaped formation material and placing cement slurry around the formation material.

9. The method according to claim 8, additionally comprising inserting formation fluids into the interior of the formation material cylinder.

10. The method according to claim 8, wherein the formation fluid and cement slurry are maintained at the same pressure while the cement hardens.

11. The method according to claim 8, wherein the formation fluid and cement slurry are maintained at the different pressures while the cement hardens.

12. The method according to claim 8, wherein the formation fluid is maintained at a pressure higher than the pressure of the cement slurry while the cement hardens.

13. The method according to claim 8, wherein the formation fluid is maintained at a pressure lower than the pressure of the cement slurry while the cement hardens.

14. An apparatus for use in testing the bonding of a cement material to a sample of formation material, comprising:
    a pressure vessel defining a sealed vessel chamber for receiving a cement slurry; and
    a formation sample in the vessel chamber, a sealed chamber formed inside the formation sample.

15. The apparatus according to claim 14, where in the formation sample is cylindrical shaped.

16. The apparatus according to claim 15, additionally comprising plugs located in the ends of the cylindrical shaped formation sample to close off the end.

17. The apparatus according to claim 15, additionally comprising a pump connected to chamber in the pressure vessel.

18. The apparatus according to claim 15, additionally comprising a pump connected to chamber in the formation sample vessel.

19. The apparatus according to claim 15, additionally comprising a piston reciprocally mounted in the chamber of the pressure vessel.

20. The apparatus according to claim 19, where in a plurality of pistons are reciprocally mounted in the chamber of the pressure vessel.

* * * * *